United States Patent [19]

Jacquot

[11] Patent Number: 5,256,829
[45] Date of Patent: Oct. 26, 1993

[54] DEBROMINATION OF DIBROMONAPHTHOLS

[75] Inventor: Roland Jacquot, Sainte Foy Les Lyon, France

[73] Assignee: Potasse et Produits Chimiques, Thann, France

[21] Appl. No.: 955,421

[22] Filed: Oct. 2, 1992

[30] Foreign Application Priority Data

Oct. 4, 1991 [FR] France ................................ 91 12268

[51] Int. Cl.$^5$ ............................................. C07C 39/38
[52] U.S. Cl. ................................... 568/737; 568/735
[58] Field of Search ............................... 568/737, 735

[56] References Cited

U.S. PATENT DOCUMENTS 2,025,032  12/1935  Arnold et al. ........................ 570/220

FOREIGN PATENT DOCUMENTS 0179447  4/1986  European Pat. Off. ............ 568/655

Primary Examiner—Werren B. Lone
Attorney, Agent, or Firm—Burns, Doane, Swecker & Mathis

[57] ABSTRACT

Dibrominated naphthol compounds, e.g., 1,6-dibromo-2-hydroxynaphthalene, are regioselectively catalytically hydromonodebrominated, e.g., into 6-bromo-2-hydroxynaphthalene, by reacting such dibromonaphthols with molecular hydrogen, or a precursor compound that generates nascent hydrogen in the medium of reaction, in an acidic organic solvent and in the presence of a catalytically effective amount of a tungsten carbide-based catalyst.

16 Claims, No Drawings

DEBROMINATION OF DIBROMONAPHTHOLS

BACKGROUND OF THE INVENTION

1. Field of the Invention

The present invention relates to the debromination of dibrominated naphthol compounds, and, more especially, to a process for the monodebromination of dibrominated naphthol compounds of formula (1):

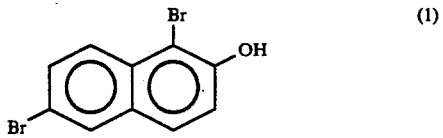

by regioselective catalytic hydrodebromination,

The particularly desired reaction products prepared by the subject debromination process of the invention have the formula (2):

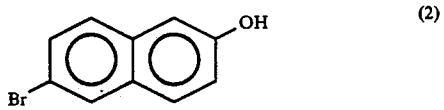

2. Description of the Prior Art

6-Bromo-2-hydroxynaphthalene (also named 6-bromo-β-naphthol) of formula (2) above is a known compound that is particularly advantageous and valuable. It is in fact used for the synthesis of 6-bromo-2-methoxynaphthalene (via alkylation by means of dimethyl sulfate or methanol), the latter compound being widely used for the production of naproxen or nabumetone, which are well-known anti-inflammatory drugs, or even methallenestril, which is an estrogen (compare, for example, the Merk Index, eleventh edition, pages 1002, 1014 and 937 (1989)).

EP-A-179,447 describes the preparation of 6-bromo-2hydroxynaphthalene by stoichiometric metallic reduction of 1,6-dibromo-2-hydroxynaphthalene, according to the following reaction scheme:

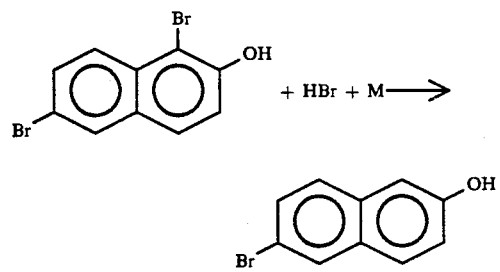

wherein M is a reducing metal, such as iron or tin, and the above dibrominated compounds may themselves be prepared simply by direct bromination or β-naphthol, as follows:

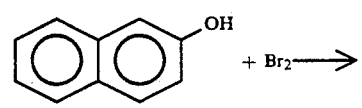

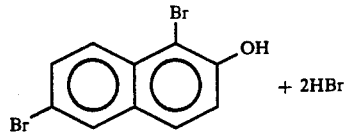

However, the reduction of dibrominated naphthol compounds to monobrominated derivatives via a process such as that described above presents the disadvantage, inter alia, of requiring a significant consumption of metal, metal which moreover reappears in the form of a waste effluent which is difficult to recover and which is sometimes polluting, such as, for example, $FeBr_2$.

In addition, the reaction yields of desired monobrominated derivatives by such a process may prove to be insufficient.

SUMMARY OF THE INVENTION

Accordingly, a major object of the present invention is the provision of an improved process for the debromination of certain dibrominated naphthol compounds which avoids the above disadvantages and drawbacks to date characterizing the state of this art, and which also permits conducting a regioselective debromination, in particular at position 1, with a high yield.

Briefly, the present invention features the debromination of dibrominated naphthol compounds, comprising reacting (i) a dibrominated naphthol compound of the formula:

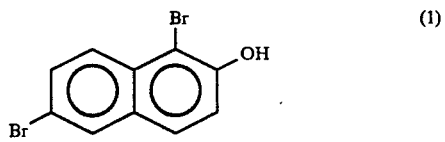

with (ii) molecular hydrogen or a compound that generates nascent hydrogen in situ in the reaction mixture, in an acidic organic solvent and in the presence of a catalytically effective amount of a tungsten carbide-based catalyst.

DETAILED DESCRIPTION OF THE PREFERRED EMBODIMENTS OF THE INVENTION

More particularly according to the present invention, in a preferred embodiment thereof, the subject process is carried out in the presence of iron and/or copper.

The process of the invention presents many advantages and a great flexibility of use. First, it permits avoiding the stoichiometric consumption of reducing metals. Moreover, quite surprisingly and unexpectedly, it is also highly selective, in the sense that, in the compounds of formula (1) above, only the bromine atom in position 1 is substituted, even in the case of using a large stoichiometric excess of hydrogen. The yields of monobrominated derivatives are high.

The reaction can additionally be carried out over a wide range of pressures and temperatures, and in a wide variety of embodiments.

It can thus be carried out in batches, semicontinuously or continuously, in a stirred reactor or in a trickling stationary bed.

- In all cases, recovery and reuse of the catalyst is permitted, which adds to economics of the process. In light of the fact that the process is being carried out under conditions of heterogeneous catalysis, the subsequent recovery of the catalyst is very easy, since it can be carried out by simple means, such as a filtration or a separation.

Finally, the process according to the invention presents the advantage that it can be carried out directly and without prior separation or purification of the reaction product obtained by direct bromination of β-naphthol.

The catalysts used in the present invention are catalysts based on tungsten carbide. These catalysts may also comprise, in addition to the tungsten carbide, one or more other metal monocarbides. Particularly exemplary such other metal monocarbides are the carbides of molybdenum, vanadium, niobium, tantalum, titanium, iron and chromium; these are widely described in the literature. The amount of these other metal carbides preferably ranges from 0.01% to 50% by weight with respect to the total amount of all carbides present.

Although tungsten carbide is itself a well-known material, it will be appreciated that its use as a hydrodebromination catalyst according to the present invention is conspicuously novel.

The catalyst is either based on bulk tungsten carbide, or based on supported tungsten carbide. Oxides, such as silica, alumina and titanium dioxide, or charcoal, are especially useful as supports.

The catalyst can thus be in the form of a monolithic substrate (honeycomb or otherwise) of tungsten carbide or of a monolithic substrate coated with a layer of tungsten carbide, or else it may be in the form of divided product& made of, or coated with, tungsten carbide. By "divided form" is meant pulverulent materials (powders) and also the articles obtained by shaping these materials (beads, pellets, spheres, granules, extrudates, agglomerates and others, with a circular, oval, trilobate or multilobate, solid or hollow cross-section).

The catalysts of the bead, pellet and other type present the advantage of permitting subsequent separation, very rapidly, from the react ion mixture by simple decanting. The catalysts of the pulverulent type generally require a filtration stage for their separation.

All of the above catalysts are, of course, selected with a specific surface area which is suitable for the application under consideration. In practice, a tungsten carbide can be used whose specific surface area (BET) ranges from 0.1 to several hundreds of m$^2$/g and, in particular, from 1 to 300 or 400 m$^2$/g.

To this end, either tungsten carbides which are commercially available, or tungsten carbides synthesized according to any process known per se, may be used. By way of examples, tungsten carbides having high specific surface areas can be manufactured according to the process described in published application PCT/FR-90/00,204.

The amount of catalyst to be used is not critical and can vary over wide limits; 0.01% to 50% by weight of catalyst with respect to the amount of dibrominated starting compound is typically used.

It is also within the scope of this invention to introduce small amounts of copper and/or iron into the reaction mixture, with a view towards substantially improving the yields of desired monobrominated compound. These elements can be introduced in the metallic state or in the form of a salt which is soluble in the reaction mixture. The amount, in moles, of iron and/or copper which is generally used then ranges from 0.01 to 0.1 times the amount in moles of dibrominated starting compound. It will also be appreciated that such amounts are considerably less than the stoichiometric amounts which are required in accordance with the process of the above EP-A-179,447. In contradistinction to the catalyst based 6n tungsten carbide, the iron and/or copper is consumed during the reaction.

According to the present invention, it is required that the reaction be carried out in a solvent medium.

It has thus been determined that the selection of the solvent to be used is of particular importance and that this selection is limited to organic solvents and, more particularly, to acidic organic solvents.

As utilized herein, by the term "acidic organic solvents" are intended either (a) protic organic solvents selected from among the simple or functionalized carboxylic acids; or (b) aprotic organic solvents comprising at least one organic or inorganic acid.

Indeed, it has been determined that the protic organic solvents of the alcohol type are not suitable for carrying out the process of the present invention.

The preferred organic solvents according to this invention are the simple or functionalized carboxylic acids, the aromatic hydrocarbons and the halogenated hydrocarbons, ethers and esters.

Exemplary carboxylic acids which are suitable solvents per the present invention include methanoic, ethanoic, propanoic, butanoic and trifluoroacetic acid. The term "carboxylic acids" also comprehends the simple or functionalized polycarboxylic acids generically, provided that they are liquid under the conditions of the reaction.

Exemplary of the preferred aprotic organic solvents are, inter alia, (i) such aromatic hydrocarbons as benzene and the alkylbenzenes (ethyl-, butyl- or propylbenzene, and the like), toluene and the xylenes; (ii) such halogenated, preferably fluorinated and chlorinated hydrocarbons, of paraffinic, cycloparaffinic and aromatic type, as dichloromethane, 1,2-dichloroethane and chlorobenzene; (iii) such ethers as, especially, isopropyl ether; and (iv) such esters as, especially, the acetates and benzoates, in particular the alkyl esters, for example ethyl acetate or methyl benzoate.

It will of course also be appreciated that mixtures of carboxylic acids, or mixtures of aprotic organic solvents, or mixtures of carboxylic acids with aprotic organic solvents, constitute suitable solvents according to the present invention.

Exemplary acids, whether used alone or in admixture, that can be contained in the aprotic organic solvents such as indicated above, include such inorganic acids as phosphoric acid, sulfuric acid and the halo acids, for example hydrochloric acid or hydrobromic acid; and such organic acids as the above-mentioned carboxylic acids and methanesulfonic, triflic, ethanesulfonic or benzenesulfonic, oxalic, malonic, succinic, glutaric, adipic, maleic, fumaric, phthalic and mellitic acid.

The amount of acid, in moles, comprising the aprotic organic solvent typically ranges from 0.1 to 5 times the amount in moles of dibrominated starting compounds, preferably ranging from 0.1 to 2 times this amount.

The amount of hydrogen to be used can vary over wide limits; it must nevertheless correspond at the very least to the stoichiometric amount required to permit complete substitution of half the bromine atoms which were present on the starting material dibrominated compound. There is no upper limit on the amount to be introduced.

According to the invention, hydrogen is preferably employed in the gaseous molecular state ($H_2$). It is nevertheless also possible to use nascent hydrogen, namely, hydrogen formed in situ in the reaction mixture by decomposition of a precursor compound, such as a formate or formic acid.

The temperatures at which the reaction is carried out can vary over very wide limits.

The reaction can thus be carried out from room temperature up to, theoretically, the boiling point of the solvent which is being used, while taking care, however, not to exceed temperatures where the dibrominated derivative and/or the reaction product likely would decompose; in actual practice, the reaction is generally carried out at temperatures ranging from 20° C. to 200° C., and preferably from 50° to 150° C.

The reaction can be carried out either at atmospheric pressure in an open-type reactor, or a trickling stationary bed, into which a continuous stream of hydrogen is sparged or, preferably, under autogenous pressure in a closed reactor of the autoclave type, containing a hydrogen atmosphere. In the latter event, the hydrogen pressure can range from 1 to 50 bars and, preferably, from 5 to 20 bars.

The reaction is preferably carried out with stirring, generally until complete or virtually complete disappearance of the dibrominated naphthol starting reactant.

At the end of the reaction, the monobrominated compound final product is separated from the reaction is mixture by any means known per se, such as, for example, filtration, density separation, centrifugation, extraction or distillation.

Thus, for example, the recovery of the catalysts may first be carried out, especially by filtration or decanting, followed by separation of the monobrominated compound and the organic solvent phase, for example by extraction with water or distillation.

The catalysts and/or the solvents thus recovered, optionally after purification, can then be recycled to the start of the process.

The monobrominated compound recovered can, in turn, be subjected to additional purification stages, if necessary.

In order to further illustrate the present invention and the advantages thereof, the following specific examples are given, it being understood that same are intended only as illustrative and in nowise limitative.

In said examples to follow, DC denotes the Degree of Conversion, namely, the ratio:

$$\frac{\text{Quantity in moles of dibrominated compound converted}}{\text{Quantity in moles of dibrominated compound introduced}} \times 100$$

RY denotes the Reaction Yield with respect to a given reaction product, namely, the ratio:

$$\frac{\text{Quantity in moles of product formed}}{\text{Quantity in moles of dibrominated compound introduced}} \times 100$$

RS expresses the selectivity of the reaction for a given reaction product, and is defined by the ratio: RY/DC.

EXAMPLE 1

Use of a WC catalyst alone

Introduced into a 35 ml glass flask were 1.2 g of 1,6-dibromo-2-naphthol, 0.47 g of a tungsten carbide WC powder (mean particle size: 1 μm, specific surface area: 1.6 m$^2$/g), and 15 ml of acetic acid.

The open flask was then placed into a 125 ml autoclave (Hastelloy C). The autoclave was then purged two times with nitrogen at a pressure of 15 bar and then two times with hydrogen at 10 bar.

20 bars of hydrogen were then introduced into the autoclave and the latter was heated for 4 hours at 100° C. with stirring. At the end of the reaction, the autoclave was cooled, the glass flask was removed, the tungsten carbide separated out and the organic phase was withdrawn.

An analysis by GPC (gas phase chromatography) determination with an internal standard provided the following results:

|  |  |
|---|---|
|  | DC = 83% |
| 6-Bromo-2-naphthol: | RY = 73% |
| 6-Bromo-2-naphthol acetate: | RY = 6% |
| 1-Bromo-2-naphthol: | RY = 3% |

EXAMPLE 2

Use of WC+Copper

Introduced into a 35 ml glass flask were 1.2 g of 1,6-dibromo-2-naphthol, 40 mg of WC powder, 12 mg of metallic copper and 15 ml of acetic acid.

The reaction was then carried out as in Example 1.

The GPC analysis provided the following results:

|  |  |
|---|---|
|  | DC = 98% |
| 6-Bromo-2-naphthol: | RY = 79% |
| 1-Bromo-2-naphthol: | RY = 4% |
| 6-Bromo-2-naphthol acetate: | RY = 8% |

EXAMPLE 3

Use of WC+Iron

Introduced into a 300 ml Sotelem were 20 g of 1,6-dibromo-2-naphthol, 1.29 g of a WC powder, 0.184 g of metallic iron as a powder and 100 ml of acetic acid.

The reaction was then carried out as in Example 1, except that the heating at 100° C. was maintained for only 1 hour, 30 minutes.

The GPC analysis provided the following results:

|  |  |
|---|---|
|  | DC = 97% |
| 6-Bromo-2-naphthol: | RY = 81% |
| 6-Bromo-2-naphthol acetate: | RY = 13% |
| 1-Bromo-2-naphthol: | RY = 2% |

EXAMPLE 4

Use of WC alone

Introduced into a 300 ml Sotelem were 100 ml of chlorobenzene, 4 g of hydrobromic acid, 30 g of 1,6-dibromo-2-naphthol and 9.7 g of WC powder.

The reaction was then carried out as in Example 1, except that the heating at 100° C. was maintained for only 3 hours.

The GPC analysis provided the following results:

|  |  |
|---|---|
|  | DC = 100% |

| 6-Bromo-2-naphthol: | RY = 96% |

EXAMPLE 5

Use of WC alone

Introduced into a 300 ml Hastelloy reactor were 100 ml of isopropyl ether, 1.6 g of hydrobromic acid, 30 g of 1,6-dibromo-2-naphthol and 4.8 g of WC as a powder. The reactor was then purged two times with nitrogen at a pressure of 10 bar and then three times with hydrogen at 10 bar. The reactor was heated at 120° C. for 6 hours under 20 bar of hydrogen while stirring the mixture.

The GPC analysis provided the following results:

| 6-Bromo-2-naphthol: | DC = 87% |
| | RY = 83% |

EXAMPLE 6

Introduced into a 35 ml glass flask were 1.5 g of 1,6-dibromo-2-naphthol, 10 ml of ethyl acetate, 0.2 g of hydrobromic acid and 0.4 g of WC powder.

The reaction was then carried out as in Example 1.
The GPC analysis provided the following results:

| 6-Bromo-2-naphthol: | DC = 23% |
| | RY = 90% |

EXAMPLE 7

Use of a mixture of carbides (WC+VC)

Introduced into a 35 ml glass flask were 1.5 g of 1,6-dibromo-2-naphthol, 10 ml of toluene, 0.3 g of hydrobromic acid and 0.48 g of a mixed carbide of tungsten and vanadium as a powder (the vanadium constituted 0.26% of the total weight of the carbides).

The open flask was then introduced into a 125 ml Hastelloy HB2 autoclave. The autoclave was then purged two times with nitrogen at a pressure of 15 bar and then 2 times with 2 times 10 bar of hydrogen.

The autoclave was then placed under 20 bar of hydrogen and this pressure was maintained for the entire duration of the reaction, with stirring and while maintaining the temperature at 120° C. After 4 hours of reaction, the glass flask was removed and the carbide was decanted or filtered.

The organic phase was drawn off.
The GPC analysis provided the following results:

| 6-Bromo-2-naphthol: | DC = 89% |
| | RY = 86% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the monodebromination of a dibrominated naphthol compound, comprising reacting (i) a dibrominated naphthol compound having the formula (1):

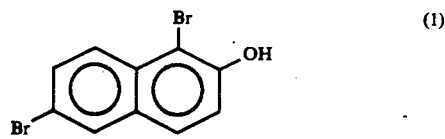

with (ii) molecular hydrogen or a precursor compound that generates nascent hydrogen in the medium of reaction, in an acidic organic solvent and in the presence of a catalytically effective amount of a tungsten carbide-based catalyst.

2. The process as defined by claim 1, said tungsten carbide-based catalyst comprising at least one other metal carbide.

3. The process as defined by claim 1, said tungsten carbide-based catalyst being in a divided state.

4. The process as defined by claim 1, said tungsten carbide-based catalyst having a specific surface area ranging from 1 to 400 m²/g.

5. The process as defined by claim 1, said tungsten carbide-based catalyst comprising at least one of iron and copper values.

6. The process as defined by claim 5, wherein the amount, in moles, of said at least one of iron and copper values ranges from 0.01 to 0.1 times the amount in moles of the starting dibrominated naphthol compound (1).

7. The process as defined by claim 1, comprising reacting molecular hydrogen, $H_2$, with said dibrominated naphthol compound (1).

8. The process as defined by claim 1, comprising reacting a nascent hydrogen precursor with said dibrominated naphthol compound (1).

9. The process as defined by claim 1, carried out under pressure.

10. The process as defined by claim 1, said dibrominated naphthol compound (1) comprising the product of the direct bromination of 2-naphthol.

11. The process as defined by claim 1, said acidic organic solvent medium comprising a simple or functionalized monocarboxylic or polycarboxylic acid.

12. The process as defined by claim 1, said acidic organic solvent medium comprising an aprotic organic solvent containing an organic or inorganic acid.

13. The process as defined by claim 12, said aprotic organic solvent comprising an aromatic or halogenated hydrocarbon, an ether or an ester.

14. The process as defined by claim 3, said tungsten carbide-based catalyst comprising a powder.

15. The process as defined by claim 8, said nascent hydrogen precursor comprising formic acid or a formate.

16. The process as defined by claim 2, said at least one other metal carbide comprising a carbide of molybdenum, vanadium, niobium, tantalum, titanium, iron or chromium.

* * * * *